US010751441B2

(12) United States Patent
Bender et al.

(10) Patent No.: US 10,751,441 B2
(45) Date of Patent: Aug. 25, 2020

(54) TISSUE-ADHESIVE POROUS HAEMOSTATIC PRODUCT

(71) Applicant: GATT Technologies B.V., Nijmegen (NL)

(72) Inventors: Johannes Caspar Mathias Elizabeth Bender, Overasselt (NL); Marcel Alexander Boerman, Utrecht (NL)

(73) Assignee: GATT TECHNOLOGIES B.V., Nijmegen (NL)

( * ) Notice: Subject to any disclaimer, the term of this patent is extended or adjusted under 35 U.S.C. 154(b) by 0 days.

(21) Appl. No.: 16/226,374

(22) Filed: Dec. 19, 2018

(65) Prior Publication Data
US 2019/0125922 A1 May 2, 2019

Related U.S. Application Data

(62) Division of application No. 15/516,467, filed as application No. PCT/NL2015/050696 on Oct. 5, 2015, now Pat. No. 10,232,077.

(30) Foreign Application Priority Data

Oct. 6, 2014 (EP) .................................... 14187781

(51) Int. Cl.
*A61L 15/26* (2006.01)
*A61P 7/04* (2006.01)
*A61L 15/32* (2006.01)
*A61L 15/42* (2006.01)
*A61L 15/58* (2006.01)

(52) U.S. Cl.
CPC ............. *A61L 15/26* (2013.01); *A61L 15/325* (2013.01); *A61L 15/425* (2013.01); *A61L 15/58* (2013.01); *A61L 2400/04* (2013.01)

(58) Field of Classification Search
CPC ........ A61L 15/26; A61L 15/58; A61L 15/325; A61L 15/425; A61L 2400/04
See application file for complete search history.

(56) References Cited

U.S. PATENT DOCUMENTS

| 3,996,237 A | 12/1976 | Tomalia |
| 5,614,587 A | 3/1997 | Rhee et al. |
| 5,635,571 A * | 6/1997 | Frechet ................. C08F 290/06 525/410 |
| 6,566,406 B1 | 5/2003 | Pathak et al. |
| 9,416,228 B2 | 8/2016 | Bender et al. |
| 9,770,527 B2 | 9/2017 | Hoogenboom et al. |
| 2002/0042473 A1 | 4/2002 | Trollsas et al. |
| 2003/0119985 A1 | 6/2003 | Sehl et al. |
| 2004/0157157 A1 | 8/2004 | Saito et al. |
| 2005/0002893 A1 | 1/2005 | Goldmann |
| 2006/0258560 A1 * | 11/2006 | Yang ..................... A61L 24/043 514/17.2 |
| 2010/0069579 A1 | 3/2010 | Harris et al. |
| 2011/0123453 A1 | 5/2011 | Bentley et al. |
| 2011/0251574 A1 * | 10/2011 | Hedrich ............... A61L 24/0036 604/368 |
| 2012/0041481 A1 | 2/2012 | Daniloff et al. |
| 2013/0345334 A1 * | 12/2013 | Hoogenboom ......... A61L 27/18 523/118 |

FOREIGN PATENT DOCUMENTS

| GB | 0 760 311 A | 10/1956 |
| GB | 1 164 582 A | 9/1969 |
| JP | 2005-161698 A | 6/2005 |
| WO | WO-00/33764 A1 | 6/2000 |
| WO | WO-00/71600 A1 | 11/2000 |
| WO | WO-02/062276 | 8/2002 |
| WO | WO-02/102864 A1 | 12/2002 |
| WO | WO-2004/028404 | 4/2004 |
| WO | WO-2005/109248 | 11/2005 |
| WO | WO-2006/034128 A2 | 3/2006 |
| WO | WO-2006/078282 A2 | 7/2006 |
| WO | WO-2009/043027 A2 | 4/2009 |
| WO | WO-2009/089542 A2 | 7/2009 |

(Continued)

OTHER PUBLICATIONS

Rosa; title: Poly(2-oxazoline)s as materials for biomedical applications; Journal of Materials Science Materials in Medicine, published online Aug. 23, 2013. (Year: 2013).*
Kelly AM, et al; title: Synthesis of poly(2-oxazoline)-based hydrogels with tailor-made swelling degrees capable of stimuli-triggered compound release; Macro-mol Rapid Commun. 2011; vol. 32, No. 22; pp. 1815-1819; Epub Sep. 20, 2011. (Year: 2011).*
International Search Report issued in International Patent Application No. PCT/NL2015/050696, dated Mar. 24, 2016.
Bentolila et al., "Poly(N-acryl amino acids): A New Class of Biologically Active Polyanions", Journal of Medicinal Chemistry, American Chemical Society, vol. 43, 2000, pp. 2591-2600 (10 pages).
Cesana et al., "First poly(2-oxazoline)s with Pendant Amino Groups," Macromolecular Chemistry and Physics, 2006, vol. 207, pp. 183-192 (10 pages).

(Continued)

*Primary Examiner* — Yanzhi Zhang
(74) *Attorney, Agent, or Firm* — Foley & Lardner LLP

(57) ABSTRACT

A process of preparing an adhesive haemostatic product is provided. The process comprises: (a) coating a porous solid substrate with a coating liquid that comprises an electrophilically activated polyoxazoline (EL-POX) and a solvent to produce a coated substrate; and (b) removing the solvent from the coated substrate. The EL-POX comprises at least 2 reactive electrophilic groups. The process enables the application of an EL-POX coating that leaves the pore structure of the substrate largely intact so that the ability of the porous substrate to absorb body fluids, such as blood, remains essentially unaffected. The EL-POX coated haemostatic product obtained by the present process has excellent adhesive properties due to the presence of electrophilic reactive groups that are capable of reacting with e.g. amine groups that are naturally present in tissue, under the formation of covalent bonds.

20 Claims, No Drawings

(56) References Cited

FOREIGN PATENT DOCUMENTS

| WO | WO-2009/112402 A1 | 9/2009 |
| WO | WO-2010/033207 A1 | 3/2010 |
| WO | WO-2010/043979 A2 | 4/2010 |
| WO | WO-2010/059280 | 5/2010 |
| WO | 2012/057628 A2 * | 5/2012 |
| WO | WO-2012/057628 A2 | 5/2012 |

OTHER PUBLICATIONS

Chujo et al. "Reversible Gelation of Polyoxazoline by Means of Diels-Alder Reaction", Macromolecules, 1990, vol. 23, pp. 2636-2641 (6 pages).

Diehl et al., "Thermo-responsive Polyoxazolines with Widely Tuneable LCSTa", Macromolecular Bioscience, Feb. 2009, vol. 9, No. 2, pp. 157-161 (5 pages).

Inata et al., "Postcrosslinking of ILnear Polyesters. II. UV-Induced Crosslinking Agents Having Carboxyl Reactive Group", Journal of Applied Polymer Science, vol. 36, 1988, pp. 1667-1672 (6 pages).

International Search Report for PCT/NL2012/050933 dated May 7, 2013 (4 pages).

International Search Report for PCT/NL2013/050187 dated Apr. 25, 2013 (2 pages).

International Search Report in PCT/NL2012/050001 dated May 16, 2012.

Liu et al., "Shell Cross-Linked Micelle-Based Nanoreactors for the Substrate-Selective Hydrolytic Kinetic Resolution of Epoxides", Journal of American Chemical Society, 2011, vol. 133, pp. 14260-14263, (4 pages).

Luxenhofer, Robert, "Novel Functional Poly(2-oxazoline)s as Potential Carriers for Biomedical Applications", Dissertation, Technische Universitat Munchen, Jun. 26, 2007 (311 pages).

Luxenhofer, Robert, "Novel Functional Poly(2-oxazoline)s as Potential Carriers for Biomedical Applications", Dissertation, Technische Universitat Munchen, Jun. 26, 2007, pp. 167-173, 248 (13 pages).

Mero et al., "Synthesis and characterization of poly(2-ethyl 2-oxazoline)-conjugates with proteins and drugs: Suitable alternatives to PEG-conjugates?", Journal of Controlled Release, 2008, vol. 125, pp. 87-95 (9 pages).

Richter et al., "Uber die Umsetzungen von 2-Alkyl-Delta2-oxazolinen und 2-Methyl-Delta2-thiazolin mit Arylisocyanaten", Liebigs Ann. Chem., vol. 743, 1971, pp. 10-24 (15 pages).

Santini et al., "Synthesis and Bulk Assembly Behavior of Linear-Dendritic Rod Diblock Copolymers", Journal of Polymer Science: Part A: Polymer Chemistry, 2004, vol. 42, pp. 2784-2814 (31 pages).

Zarka, et al. "Amphiphilic Polymer Supports for the Asymmetric Hydrogenation of Amino Acid Precursors in Water", Chem. Eur. J., 2003, vol. 9, pp. 3228-3234 (7 pages).

* cited by examiner

TISSUE-ADHESIVE POROUS HAEMOSTATIC PRODUCT

CROSS-REFERENCE TO RELATED APPLICATIONS

This application is a Division of U.S. application Ser. No. 15/516,467, filed Apr. 3, 2017, which is the National Phase of International Patent Application No. PCT/NL2015/050696, filed Oct. 5, 2015, published on Apr. 14, 2016 as WO 2016/056901 A1, which claims priority to European Patent Application No. 14187781.1, filed Oct. 6, 2014. The contents of these applications are herein incorporated by reference in their entirety.

TECHNICAL FIELD OF THE INVENTION

The invention relates to a tissue-adhesive haemostatic product comprising a porous solid substrate and a coating that contains an electrophilically activated polyoxazoline (EL-POX). This new haemostatic product exhibits excellent biodegradability, adhesiveness and haemostatic properties. Examples of haemostatic products encompassed by the present invention include haemostatic meshes, haemostatic foams and haemostatic powders.

Also provided is a process for preparing a tissue-adhesive haemostatic product which involves coating a porous solid substrate with an electrophilically activated polyoxazoline (EL-POX).

BACKGROUND OF THE INVENTION

Wound dressings form an important segment of the global wound care market. These products are widely used in the treatment of injuries such as wounds, hemorrhages, damaged tissues, and bleeding tissues. The ideal dressing should prevent excessive bleeding and promote rapid healing at a reasonable cost with minimal inconvenience to the patient.

The haemostatic properties of a wound dressing are determined by the texture and the porosity of the material. As regards porosity, the pores of the dressing are usually so tiny that they are not visible to the human eye upon casual inspection. They are, however, of sufficient size not only to permit ample transpiration of skin moisture and wound vapors, but also to permit absorption of blood so that the dressing becomes firmly anchored to the tissue once the blood has coagulated.

Wound dressings should be able to maintain a moist environment around the wound, effective oxygen circulation to aid regeneration of cells and tissue, and a low bacterial load. Wound dressings that are employed during surgery and that remain in the body should be biodegradable and completely resorbable.

Conventional tissue-adhesive wound dressings include fibrin sealants, cyanoacrylate based sealants, and other synthetic sealants and polymerizable monomers. These tissue-adhesives are only suitable for specific applications because of several drawbacks, including release of toxic degradation products, high cost, need for refrigerated storage, slow curing, limited mechanical strength and risk of infection. Therefore, hydrogel tissue adhesives have been developed on the basis of reactive polyethylene glycol (PEG) precursors. However, these hydrogel tissue adhesives swell or dissolve away too quickly, or lack sufficient cohesion, thereby decreasing their effectiveness as surgical adhesive. Moreover, the properties of such PEG-based material cannot be easily controlled.

Haemostatic powders are another example of a haemostatic product that is widely used. Examples of commercially available haemostatic powers, also known as styptic powders, include an adsorbable haemostatic gelatin powder (Spongostan® powder) and a calcium-loaded form of zeolite also known as QuikClot®. These haemostatic powders can be used to stop severe bleeding.

U.S. Pat. No. 5,614,587 describes collagen-based compositions useful in the attachment of tissues, or the attachment of tissues to synthetic implant materials. The compositions comprise fibrillar collagen, a fiber disassembly agent, and a multifunctionally activated synthetic hydrophilic polymer such as polyethylene glycol, wherein the collagen and synthetic polymer covalently bind to form a collagen-synthetic polymer conjugate.

WO 2004/028404 describes a tissue sealant composed of a synthetic collagen or synthetic gelatin and a electrophilic cross-linking agent which are provided in a dry state. In this international publication the crosslinker comprises an electrophilically activated (EA) poly (ethylene glycol) (PEG) or an EA PEG derivative such as PEG-succinimidyl ester, in particular PEG-succinimidyl propionate, PEG-succinimidyl butanoate, or PEG-succinimidyl glutarate. Upon wetting of this composition at an appropriate pH a reaction between the 2 components takes place and a gel with sealing properties is formed.

US 2011/0251574 describes a haemostatic porous composite sponge comprising a matrix of a biomaterial and a hydrophilic polymeric component comprising reactive groups wherein said polymeric component is coated onto a surface of said matrix of a biomaterial, or said matrix is impregnated with said polymeric material, or both. In a preferred embodiment the polymer is a polyalkylene oxide polymer, more particularly a multi-electrophilic polyethylene glycol (PEG). The matrix material can be selected from collagen, gelatin, fibrin, a polysaccharide (such as chitosan), a synthetic biodegradable biomaterial (such as polylactic acid or polyglycolic acid), and derivatives thereof.

US 2010/069579 a terminally activated polyoxazoline (POZ) compound, said POZ compound comprising a POZ polymer having a single active functional group on a terminal end thereof, said functional group capable of reacting with a group on a target molecule to create a target molecule-POZ conjugate wherein all the linkages between the target molecule and the POZ compound are hydrolytically stable linkages.

WO 2012/057628 describes crosslinked polyoxazoline polymers having tissue-adhesive properties due to the presence of electrophilic groups that are capable of reacting with nucleophile-containing chemical entities present in natural tissue.

It is an object of the present invention to provide a tissue-adhesive haemostatic product with improved properties.

SUMMARY OF THE INVENTION

The inventors have discovered that a tissue-adhesive haemostatic product having improved properties can be produced by a process that comprises to following steps:
  providing a porous solid substrate;
  coating the substrate with a coating liquid that comprises an electrophilically activated polyoxazoline (EL-POX) and a solvent to produce a coated substrate, said EL-POX containing at least 2 reactive electrophilic groups;
  removing the solvent from the coated substrate.

The inventors have surprisingly found that EL-POX can be applied onto a porous solid substrate by means of the present method without adversely affecting the porous structure of the substrate. The present process enables the application of an EL-POX coating that leaves the pore structure of the substrate largely intact so that the ability of the porous substrate to absorb body fluids, such as blood, remains essentially unaffected. The EL-POX coated haemostatic product obtained by the present process has excellent adhesive properties due to the presence of electrophilic reactive groups that are capable of reacting with e.g. amine groups that are naturally present in tissue, under the formation of covalent bonds.

The present invention also provides a tissue-adhesive haemostatic product selected from a coated mesh, a coated foam and a coated powder, said haemostatic product comprising:
  a porous solid substrate having a porosity of at least 5 vol. % and comprising an outer surface that comprises a nucleophilic polymer containing reactive nucleophilic groups;
  an adhesive coating that covers at least a part of the solid substrate, said coating comprising an electrophilically activated polyoxazoline (EL-POX), said EL-POX containing on average at least 1 reactive electrophilic group.

The EL-POX polymer contained in the coating of the haemostatic product offers the advantage that it can carry a high number of electrophilic reactive groups due to the fact that the EL-POX polymer can contain a large number of pendant groups that each can carry one or more of such reactive groups. Thus, the adhesive properties of the haemostatic product can be optimized for a certain application by selecting an EL-POX having the optimum density of electrophilic groups. Also other properties of the EL-POX, such as hydrophilic/hydrophobic balance and lower critical solution temperature can suitably be optimized by modifying the concentration and/or properties of the pendant groups.

DETAILED DESCRIPTION THE INVENTION

Accordingly, one aspect of the invention relates to a process of preparing a tissue-adhesive haemostatic product, said process comprising the steps of:
  providing a porous solid substrate;
  coating the substrate with a coating liquid that comprises an electrophilically activated polyoxazoline (EL-POX) and a solvent to produce a coated substrate, said EL-POX containing at least 2 reactive electrophilic groups;
  removing the solvent from the coated substrate.

As used herein, the term "tissue-adhesive" refers to the ability of the haemostatic product to cling to tissue due to the formation of covalent bonds between said product and the tissue. In case of the present tissue adhesive haemostatic product adhesion to tissue may require the presence of water.

The term "porous" as used herein, unless otherwise indicated, means that the haemostatic product comprises pores and/or interstices that admit the entry of liquid into the product.

The term "porosity" refers to a measure of the void (i.e., "empty") spaces in the substrate or the haemostatic product, and is percentage volume of voids over the total volume. The porosity of the haemostatic products of the present invention can suitably be determined by methods known in the art, such as gas adsorption analysis. Gas adsorption analysis involves exposing solid porous materials to gases or vapors at a variety of conditions and evaluating either the weight uptake or the change in sample volume. Analysis of these data provides information regarding the physical characteristics of the solid including: skeletal density, porosity and total pore volume. Skeletal density is typically evaluated by helium pycnometry experiments and represents the true solid density of a material when there is no closed porosity. It should be understood that in case the substrate is composed of more than one item, porosity refers to the average porosity of the individual items. Thus, if the substrate is a porous powder, porosity equals the percentage of the volume of the porous particles that is occupied by pores.

The term "mean pore size" as used herein refers to the mean pore diameter as determined by scanning electron microscopy (SEM). A suitable method is described in Faraj et al., Tissue Engineering, 2007, 13, 10, 2387-2394.

The term "water absorption capacity" as used herein is a measure of the capability of the porous solid substrate to absorb water. The water absorption capacity of the porous solid substrate is determined by weighing a sample of the dry porous substrate (weight=$W_d$) followed by immersion of the porous substrate into distilled water (37° C.) for 45 minutes. Next, the sample is removed from the water and water clinging to the outside of the substrate is removed, following which the sample is weighed again (weight=$W_w$). The water absorption capacity=$100\% \times (W_w - W_d)/W_d$. The water adsorption capacity is indicative of the porosity of the substrate as well as of its ability to swell in the presence of water.

The term "polyoxazoline" as used herein refers to a poly(N-acylalkylenimine) or a poly(aroylalkylenimine) and is further referred to as POX. An example of POX is poly(2-ethyl-2-oxazoline). The term "polyoxazoline" also encompasses POX copolymers.

The term "electrophilic group" refers to a functional group that is susceptible to nucleophilic attack from a nucleophilic group and that is capable of reacting with such a nucleophilic group under the formation of a covalent bond. Electrophilic groups are typically positively charged and/or electron/deficient.

The term "nucleophilic group" refers to a functional group that is susceptible to electrophilic attack from an electrophilic group and that is capable of reacting with an electrophilic group under the formation of a covalent bond. Nucleophilic groups typically are electron rich, having an unshared pair of electrons acting as a reactive site.

The term "activated", unless otherwise indicated, refers to a modification of a polymer to generate or introduce a new reactive functional group wherein the new reactive functional group is capable of undergoing reaction with another functional group to form a covalent bond.

The term "cross-linked" as used herein refers to components such as polymers which are intermolecularly bound by covalent bonds. Covalent bonding between two crosslinkable components may be direct, or indirect through a linking group.

The term "buffering system" as used herein refers to a substance or a combination of substances that can be used in aqueous systems to drive a solution to a certain buffering pH and wherein the buffering system has a capacity to prevent change in this buffering pH.

The "buffering pH" of a liquid as used herein refers to the pH value at 20° C. measured after the liquid has been diluted 10 times with distilled water.

The "buffer capacity" as used herein refers to the capability of liquid to resist changes in pH. The buffer capacity β of a liquid (coating liquid or buffering liquid) is measured at 20° C. after 10 times dilution with distilled water and expressed in mmol·l⁻¹·pH⁻¹. The buffer capacity is defined as follows:

$$\beta = \frac{dn}{d(p[H^+])}$$

where dn is an infinitesimal amount of added base and d(p[H⁺]) is the resulting infinitesimal change in the cologarithm of the hydrogen ion concentration.

The EL-POX employed in accordance with the present invention is preferably derived from a polyoxazoline whose repeating units are represented by the following formula (I):

(CHR¹)$_m$NCOR²

R², and each of R¹ independently being selected from H, optionally substituted $C_{1-22}$ alkyl, optionally substituted cycloalkyl, optionally substituted aralkyl, optionally substituted aryl; and m being 2 or 3.

According to a preferred embodiment, the polyoxazoline is a polymer, even more preferably a homopolymer of 2-alkyl-2-oxazoline, said 2-alkyl-2-oxazoline being selected from 2-methyl-2-oxazoline, 2-ethyl-2-oxazoline, 2-propyl-2-oxazoline, 2-butyl-2-oxazoline and combinations thereof. Preferably, the polyoxazoline is a homopolymer of 2-propyl-2-oxazoline and more preferably of 2-ethyl-oxazoline.

EL-POX can carry electrophilic groups in its side chains (also referred to as pendant electrophilic groups), at its termini, or both. An example of a terminal, end capped, EL-POX is a succinimidyl succinate ester like CH₃O—POX—O₂C—CH₂—C(CH₂CO₂—NHS)₃. An example of a side chain activated EL-POX is POX containing NHS groups in the alkyl side chain. Yet another example of EL-POX are star-shaped POX-polymers end-functionalized with an NHS-esters.

The electrophilic groups present in the EL-POX are preferably selected from: carboxylic acid esters, sulfonate esters, phosphonate esters, pentafluorophenyl esters, p-nitrophenyl esters, p-nitrothiophenyl esters, acid halide groups, anhydrides, ketones, aldehydes, isocyanato, thioisocyanato (isothiocyanato), isocyano, epoxides, activated hydroxyl groups, olefins, glycidyl ethers, carboxyl, succinimidyl esters, succinimidyl carbonates, succinimidyl carbamates, sulfosuccinimidyl esters, sulfosuccinimidyl carbonates, maleimido (maleimidyl), ethenesulfonyl, imido esters, aceto acetate, halo acetal, orthopyridyl disulfide, dihydroxy-phenyl derivatives, vinyl, acrylate, acrylamide, iodoacetamide and combinations thereof. More preferably, the electrophilic groups present in the EL-POX are selected from: carboxylic acid esters, acid chloride groups, anhydrides, ketones, aldehydes, isocyanato, thioisocyanato, epoxides, activated hydroxyl groups, olefins, carboxyl, succinimidyl ester, succinimidyl carbonate, succinimidyl carbamates, sulfosuccinimidyl ester, sulfosuccinimidyl carbonate, maleimido, ethenesulfonyl and combinations thereof. Even more preferably, the electrophilic groups present in the EL-POX are selected from aldehydes, isocyanato, thioisocyanato, succinimidyl ester, sulfosuccinimidyl ester, maleimido and combinations thereof. Most preferably, the electrophilic groups present in the EL-POX are selected from isocyanato, thioisocyanato, succinimidyl ester, sulfosuccinimidyl ester, maleimido and combinations thereof.

Examples of sulfonate esters that can be used as electrophilic groups include mesylate, tosylate, nosylate, triflate and combinations thereof. Examples of olefins that can be employed include acrylate, methacrylate, ethylacrylate and combinations thereof. Examples of activated hydroxyl groups include hydroxyl groups that have been activated with an activating agent selected from p-nitrophenyl chlorocarbonates, carbonyldiimidazoles (e.g. 1,1-carbonyl diimidazole) and sulfonyl chloride.

The EL-POX employed in the present method preferably contains at least 10 reactive electrophilic groups. More preferably, the EL-POX contains at least 25, even more preferably at least 35 and most preferably at least 50 reactive electrophilic groups.

The EL-POX of the present invention advantageously contains one or more pendant electrophilic groups. Typically, the EL-POX contains 3 to 50 pendant electrophilic groups per 100 monomers, more preferably 4 to 35 pendant electrophilic groups per 100 monomers, even more preferably at least 5 to 25 pendant electrophilic groups per 100 monomers.

The EL-POX employed in accordance with the present invention typically has an average molecular weight in the range of 1,000 to 100,000 g/mol, more preferably of 5,000 to 50,000 and most preferably of 10,000 to 30,000 g/mol.

In one embodiment of the invention the porous solid substrate contains at least 50 wt. %, most preferably at least 80 wt. % of a polysaccharide selected from dextran, alginates, oxidized cellulose, oxidized regenerated cellulose (ORC), hydroxyethylcellulose, hydroxymethylcellulose, hyaluronic acid; and combinations thereof. In a particularly preferred embodiment the porous solid substrate contains at least 50 wt. %, most preferably at least 80 wt. % of ORC.

Cellulose is a homopolysaccharide of glucopyranose polymerized through β-glucosidic bonds. Prior to oxidation, the cellulose can remain non-regenerated with unorganized fibers or can be regenerated to form organized fibers. When cellulose fibers are treated with dinitrogen tetroxide, hydroxyl groups are oxidized into carboxylic acid groups yielding a polyuronic acid. While polyuronic acid is the main component of oxidized cellulose, nonoxidized hydroxyl groups remain as a fibrous component.

In a further embodiment of the invention the porous solid substrate comprises an outer surface that comprises a nucleophilic polymer containing reactive nucleophilic groups. Preferably, the porous solid substrate contains at least 5 wt. %, more preferably at least 10 wt. % and more preferably at least 50 wt. % of the nucleophilic polymer. Most preferably, the substrate consists of said nucleophilic polymer.

The nucleophilic polymer typically contains at least 2 nucleophilic groups, more preferably at least 10 nucleophilic groups, most preferably at least 20 nucleophilic groups.

The nucleophilic groups of the nucleophilic polymer are preferably selected from amine groups, thiol groups, phosphine groups and combinations thereof. More preferably, these nucleophilic groups are amine groups. These amine groups are preferably selected from primary amine groups, secondary amine groups and combinations thereof.

The nucleophilic polymer in the outer surface of the porous solid substrate preferably is a nitrogen rich polymer having a nitrogen content of at least 1 wt. %, more preferably of 5-10 wt. % and most preferably of 15-25 wt. %.

The nucleophilic polymer is preferably selected from protein, chitosan and synthetic or carbohydrate polymers containing reactive nucleophilic groups selected from amine, thiol, phosphine and combinations thereof. More preferably, the nucleophilic polymer is selected from collagen, chitosan and combinations thereof.

The term collagen as used herein refers to all forms of collagen including processed derivatives. Preferred collagens do not posses telopeptide regions ("atelopeptide collagen"), are soluble, and may be in fibrillar or non-fibrillar form. The collagen can be selected from the group of microfibrillar collagen, synthetic human collagen such as the type I collagen, type III collagen, or a combination of type I collagen and type III collagen. Collagen crosslinked using heat, radiation, or chemical agents such as glutaraldehyde may also be used to form particularly rigid crosslinked compositions. Dry, porous freeze dried collagen sponges are specifically preferred.

Chitosan is a biodegradable, nontoxic, complex carbohydrate derivative of chitin (poly-[134]-N-acetyl-D-glucosamine), a naturally occurring substance. Chitosan is the deacetylated form of chitin. In general, the generic term chitosan is applied when the extent of deacetylation is above 70% and the generic term chitin is used when the extent of deacetylation is insignificant, or below 20%. With less than 100% deacetylation, the chitosan polysaccharide is a linear block copolymer containing both N-acetyl-D-glucosamine and D-glucosamine monomer units.

According to one preferred embodiment, the nucleophilic groups of the nucleophilic polymer present in the surface of the porous solid substrate are amine groups and the electrophilic groups comprised in the EL-POX are selected from carboxylic acid esters, sulfonate esters, phosphonate esters, pentafluorophenyl esters, p-nitrophenyl esters, p-nitrothiophenyl esters, acid halide groups, anhydrides, ketones, aldehydes, isocyanato, thioisocyanato, isocyano, epoxides, activated hydroxyl groups, glycidyl ethers, carboxyl, succinimidyl esters, succinimidyl carbonates, succinimidyl carbamates, sulfosuccinimidyl esters, sulfosuccinimidyl carbonates, imido esters, dihydroxy-phenyl derivatives, and combinations thereof.

Examples of succinimidyl derivatives that may be employed include succinimidyl glutarate, succinimidyl propionate, succinimidyl succinamide, succinimidyl carbonate, disuccinimidyl suberate, bis(sulfosuccinimidyl) suberate, dithiobis(succinimidylpropionate), bis(2-succinimidooxy-carbonyloxy) ethyl sulfone and 3,3'-dithiobis(sulfosuccinimidyl-propionate). Examples of sulfosuccinimidyl derivatives that can be used include sulfosuccinimidyl(4-iodoacetyl)aminobenzoate, bis(sulfosuccinimidyl) suberate, sulfosuccinimidyl-4-(N-maleimidomethyl)-cyclohexane-1-carboxylate, dithiobis-sulfosuccinimidyl propionate, disulfo-succinimidyl tartarate; bis[2-(sulfo-succinimidyloxy-carbonyloxyethylsulfone)], ethylene glycol bis (sulfosuccinimiclylsuccinate), dithiobis-(succinimidyl propionate). Examples of dihydroxyphenyl derivatives include dihydroxyphenylalanine, 3,4-dihydroxyphenylalanine (DOPA), dopamine, 3,4-dihydroxyhydroccinamic acid (DOHA), norepinephrine, epinephrine and catechol.

According to another preferred embodiment, the nucleophilic groups of nucleophilic polymer in the outer surface of the porous solid substrate are thiol groups and the electrophilic groups contained in the EL-POX are selected from halo acetals, orthopyridyl disulfide, maleimides, vinyl sulfone, dihydroxyphenyl derivatives, vinyl, acrylate, acrylamide, iodoacetamide, succinimidyl ester, succinimidyl carbonate, succinimidyl carbamates, sulfosuccinimidyl ester, sulfosuccinimidyl carbonate and combinations thereof. More preferably, the electrophilic groups are selected from succinimidyl esters, halo acetals, maleimides, or dihydroxyphenyl derivatives and combinations thereof. Most preferably, electrophilic groups are selected from maleimides or dihydroxyphenyl derivatives and combinations thereof.

The porous solid substrate that is employed in the present process preferably has a porosity of at least 5 vol. %. In case the substrate is a foam or a mesh, the substrate preferably has a porosity of at least 50 vol. %, more preferably of at least 70 vol. % and most preferably of at least 85 vol. %. In case the substrate is a porous powder, porosity preferably is at least 20 vol. %, more preferably at least 50 vol. % and most preferably at least 75 vol. %.

The porous solid substrate that is employed in the present process preferably has a mean pore size of at least 2 μm. In case the substrate is a foam or a mesh, the substrate preferably has a mean pore size 5 to 500 μm, preferably of 10 to 200 μm. In case the substrate is a porous powder, the mean pore size is preferably 4 to 50 μm, more preferably 6 to 25 μm.

The porous solid substrate typically has a water absorption capacity of at least 25%, more preferably of at least 100%, even more preferably of at least 250% and most preferably of at least 1000%.

The porous solid substrate that is employed in the present process preferably is an object in the form of a mesh or a foam, said object having a shape that facilitates application of the coated substrate as a wound dressing, e.g. a sheet. Typically, the substrate has a length of 10 mm to 200 mm, a width of 5 mm to 200 mm and a thickness of 0.5 mm to 10 mm.

In one embodiment of the present invention the porous solid substrate is a mesh. An example of a mesh is a sheet or gauze made from woven or non-woven fibres. The fibres contained in the mesh are preferably made of biocompatible and biodegradable polymers, like gelatin, collagen, ORC or combinations thereof.

In another embodiment of the present invention the porous solid substrate is a solid foam, sometimes also referred to as sponges. The solid foam is preferably made of cross linked gelatin (gelfoam).

In a further embodiment of the invention the porous solid substrate is a powder. The porous powder is preferably made of gelatin or polysaccharide. Suitable polysaccharides are starch, modified starches, alginates, chitosan, dextran and combinations thereof. Most preferably, the polysaccharide employed is modified starch.

Preferably the porous powder is in the form of a free flowing, sterile powder. Advantageously, the powder is a micro porous powder.

The porous powder typically has a mass weighted average particle size in the range of 10-200 μm, more preferably of 25-100 μm and most preferably of 50-75 μm.

The coating liquid employed in the present process preferably contains at least 50 wt. %, more preferably at least 60 wt. %, most preferably at least 80 wt. % of solvent. The solvent is preferably selected from 2-propanol, ethyl alcohol, methanol, dichloromethane, acetone, anisole, 1-butanol, 2-butanol, butyl acetate, tert-butylmethyl ether, cumene, dimethyl sulfoxide, ethyl acetate, ethyl ether, ethyl formate, heptane, isobutyl acetate, isopropyl acetate, methyl acetate, 3-methyl-1-butanol, methylethylketone, methylisobutylketone, 2-methyl-1-propanol, pentane, 1-pentanol, 1-propanol, propyl acetate and combinations thereof. More preferably the solvent is selected from 2-propanol, ethyl alcohol, methanol, acetone and combinations thereof.

The coating liquid may suitably contain some water. Typically, the coating liquid contains less than 5 wt. % water, more preferably less than 1 wt. % water.

The coating liquid employed in the present process preferably contains at least 1 wt. % of EL-POX. More preferably the EL-POX content of the coating liquid is at least 5 wt. %, even more preferably at least 10 wt. % and most preferably at least 20 wt. %.

According to a preferred embodiment of the invention the porous solid substrate is coated by spraying the coating liquid onto the substrate. In accordance with a particularly preferred embodiment, the coating liquid is sprayed onto the substrate through an ultrasonic nozzle. The inventors have found that the use of an ultrasonic nozzle makes it possible to homogeneously coat the substrate with a coating liquid that contains a considerable amount of EL-POX.

Solvent can suitably be removed from the coated substrate by evaporation. Evaporation preferably is conducted under reduced pressure, e.g. at a pressure of less than 1 mbar.

Alternatively, the solvent can be removed from the coated substrate by contacting the coated substrate with a liquefied gas or a super critical fluid. Preferably, the liquefied gas or the supercritical fluid has a pressure of at least 30 bar.

In accordance with an advantageous embodiment of the present invention, the porous solid substrate comprises an outer surface that comprises a nucleophilic polymer as described herein before, and following the coating of the substrate with the coating liquid and before and/or during the removal of the solvent, the reactive electrophilic groups of the EL-POX react with the reactive nucleophilic groups of the nucleophilic polymer under formation of covalent bonds. Preferably said reaction occurs at a temperature of less than 50° C., more preferably at a temperature in the range of 15-25° C. (ambient conditions). This embodiment of the present process offers the advantage that the reaction between the reactive electrophilic groups and the reactive nucleophilic groups can occur in the absence of a buffering system.

In the present process the reactive electrophilic groups in the EL-POX may react with reactive nucleophilic groups present in the porous solid substrate and/or with nucleophilic groups present in other components that are employed in the process (e.g. nucleophilic crosslinkers). Preferably, after the removal of the solvent from the coated substrate, the EL-POX still contains on average at least one, more preferably at least 5 and most preferably at least 40 reactive electrophilic groups. These reactive electrophilic groups provide adhesive properties to the coated substrate as they can form covalent bonds with e.g. amine groups naturally present in tissue.

The coating liquid employed in the present process may contain the EL-POX in dissolved and/or dispersed form.

In accordance with one embodiment of the invention the coating liquid contains EL-POX in fully dissolved form and the coating liquid further contains a dispersed buffering system. Preferably, the coating liquid has a buffering pH in the range of 7 to 11, more preferably in the range of 8 to 10. The buffer capacity of the coating liquid preferably is at least 10 mmol·l$^{-1}$·pH$^{-1}$. More preferably, the buffer capacity is a least 25 mmol·l$^{-1}$·pH$^{-1}$, most preferably the buffer capacity is at least 50 mmol·l$^{-1}$·pH$^{-1}$.

In another embodiment of the invention the coating liquid contains EL-POX in fully dissolved form and the process comprises covering the porous solid substrate with a buffer liquid before the substrate is coated with the EL-POX containing coating liquid, said buffer liquid comprising a buffering system. Preferably, the buffer liquid has a buffering pH in the range of 7 to 11, more preferably in the range of 8 to 10. The buffer capacity of the buffer liquid preferably is at least 10 mmol·l$^{-1}$·pH$^{-1}$. More preferably, the buffer capacity is a least 25 mmol·l$^{-1}$·pH$^{-1}$, most preferably the buffer capacity is at least 50 mmol·l$^{-1}$·pH$^{-1}$. In case the buffer liquid is aqueous, the substrate is preferably dried after the covering with the buffer liquid before the coating with the coating liquid. Thus, unwanted cross-linking between the EL-POX and the substrate and decomposition of the EL-POX can be minimized. This embodiment offers the advantage that the EL-POX can penetrate the pores of the porous solid substrate and form a coating inside these pores. The buffer liquid employed in accordance with this embodiment may suitably contain a nucleophilic cross-linking agent, said nucleophilic cross-linking agent containing at least 2 reactive nucleophilic groups.

In yet another embodiment at least 80 wt. % of the EL-POX present in the coating liquid is undissolved when the coating liquid is coated on the porous solid substrate. Advantageously, besides the undissolved EL-POX the coating liquid contains a dissolved or undissolved buffering system. The coating liquid preferably has a buffering pH in the range of 7 to 11, more preferably in the range of 8 to 10. The buffer capacity of the coating liquid preferably is at least 10 mmol·l$^{-1}$·pH$^{-1}$. More preferably, the buffer capacity is a least 25 mmol·l$^{-1}$·pH$^{-1}$, even more preferably the buffer capacity is at least 50 mmol·l$^{-1}$·pH$^{-1}$. Preferably, after the coating of the substrate with the coating liquid containing undissolved EL-POX, the substrate is covered with a liquid solvent composition in which the EL-POX is soluble. This embodiment offers the advantage that the EL-POX does not enter the pores and that the EL-POX coating layer is concentrated onto the surface of the porous substrate. According to a particularly preferred embodiment, the liquid solvent composition contains a nucleophilic cross-linking agent.

Examples of nucleophilic cross-linking agents that may suitably be employed include nucleophilically activated PEG, nucleophilically activated POX, trilysine and combinations thereof.

The nucleophilic cross-linking agent preferably contains at least 3 reactive nucleophilic groups. The nucleophilic groups of the nucleophilic cross-linking agent are preferably selected from amine groups, thiol groups, phosphine groups and combinations thereof. More preferably, these nucleophilic groups are amine groups. According to a preferred embodiment, the nucleophilic groups present in the nucleophilic cross-linking agent are primary amine groups.

In one embodiment of the invention the nucleophilic cross-linking agent is a low molecular weight polyamine having a molecular weight of less than 1,000 g/mol, more preferably of less than 700 g/mol and most preferably of less than 400 g/mol. Even more preferably, the nucleophilic cross-linking agent is selected from the group of dilysine; trilysine; tetralysine; pentalysine; dicysteine; tricysteine; tetracysteine; pentacystein; oligopeptides comprising two or more amino acid residues selected from lysine, ornithine, cysteine, arginine and combinations thereof, and other amino acid residues; spermine; tris(aminomethyl)amine; arginine and combinations thereof.

According to another embodiment of the invention, the nucleophilic cross-linking agent is a high molecular weight polyamine selected from the group of: nucleophilically activated POX (NU-POX) comprising at least two amine groups; chitosan; chitosan derivatives (e.g. dicarboxy-derivatised chitosan polymers as described in WO 2009/028965), polyethyleneimines; polyvinylamine; polyallyl amine; amine-functionalized poly(meth)acrylates; polysaccharides containing amine-functional moieties such as aminoglycosides, such as 4,6-disubstituted deoxystreptamine (Kanamycin A, Amikacin, Tobramycin, Dibekacin, Gentamicin, Sisomicin, Netilmicin), 4,5-disubstituted deoxystreptamine (Neomycins B, C and Neomycin E (paromomycin)) and non-deoxystreptamine aminoglycosides, e.g. streptomycin; styrenics; polypeptides comprising two or more amino acid residues selected from lysine, ornithine, cysteine, arginine and combinations thereof, and other amino acid residues; and combinations thereof. Albumin of natural source or recombinant is an example of a polypeptide that may suitably be employed as a polypeptide. Amine-functionalized polyethylene glycol is another example of a high molecular weight polyamine that can suitably be employed as the nucleophilic cross-linking agent.

According to another preferred embodiment, the nucleophilic groups present in the nucleophilic cross-linking agent are thiol (sulfohydryl) groups.

In one embodiment of the invention the nucleophilic cross-linking agent employed in the cross-linked polymer is a low molecular weight polythiol comprising 2 or more thiol groups having a molecular weight of less than 1,000 g/mol, more preferably of less than 700 g/mol and most preferably of less than 400 g/mol. Even more preferably, the nucleophilic cross-linking agent is selected from the group of trimercaptopropane, ethanedithiol, propanedithiol, 2-mercaptoethyl ether, 2,2'-(ethylenedioxy)diethanethiol, tetra(ethylene glycol) dithiol, penta(ethylene glycol) dithiol, hexaethylene glycol dithiol; thiol modified pentaerythritol, dipentaerythritol, trimethylolpropane or ditrimethylolpropane; oligopeptides containing at least two cysteine units.

According to another embodiment of the invention, the nucleophilic cross-linking agent employed in the cross-linked polymer is a high molecular weight polythiol selected from the group of: NU-POX comprising at least two thiol groups; thiol-functionalized poly(meth)acrylates; polysaccharides containing thiol-functional moieties; styrenics; polypeptides comprising two or more thiol groups.

The nucleophilic cross-linking agent, as defined herein before, may suitably be employed in the coating liquid and/or the buffer liquid to covalently link the EL-POX to a porous solid substrate with an outer surface that comprises a polymer containing reactive electrophilic groups. Suitable polymers with electrophilic groups are poly(lactic-co-glycolic acid), chondroitin sulfate-NHS, chondroitin sulfate succinimidyl succinate, alginate-NHS, hyaluronic acid-NHS, copolymers comprising N-hydroxy succinimide carbonate containing methacrylate monomers (as described in Cengiz et al., 2010, J. of Polymer Science Part A: Polymer Chemistry, vol. 48, issue 21, 4737-4746), biological low-molecular-weight derivatives obtained by modifying at least one carboxyl group of a biological low-molecular-weight, compound having two or more carboxyl groups, with N-hydroxysuccinimide, N-hydroxysulfosuccinimide, or a derivative thereof (as described in EP1548004). Preferably, the nucleophilic cross-linking agent is employed in the coating liquid.

In another preferred embodiment of the invention, the EL-POX and the nucleophilic cross-linking agent are present in separate fluids, but coated simultaneously onto the porous solid substrate. This may suitably be achieved by using two ultrasonic spray nozzles. Accordingly, the method according to this advantageous embodiment comprises:
providing a solid porous substrate,
providing the coating liquid, comprising EL-POX in a first solvent;
providing a second liquid comprising a buffering system and/or a nucleophilic cross-linking agent, as well as a second solvent;
creating a first spray stream by passing the coating liquid through a first ultrasonic nozzle;
creating a second spray stream by passing the second liquid through a second ultrasonic nozzle;
simultaneously exposing at least a part of the surface of the solid porous solid substrate to both the first spray stream and the second spray stream to cover said part of the solid porous substrate with a coating mixture that comprises the EL-POX as well as the nucleophilic cross-linking agent and/or the buffering system;
removing the first and second solvent from the coating mixture to obtain a porous solid substrate that is at least partly coated with a dry layer containing the EL-POX and the nucleophilic cross-linking agent.

The EL-POX in this method may suitably be replaced by PVP-acrylic-acid-NHS or (poly-((N-vinylpyrrolidone)$_{50}$-co-(acrylic acid)$_{25}$-co-(acrylic acid N-hydroxysuccinimide ester)$_{25}$).

In case a nucleophilic cross-linking agent is employed in the above described dual spray method, the EL-POX and the nucleophilic cross-linking agent may react with each other to form a cross-linked polymer before, during or after removal of the solvents. In a preferred embodiment, the cross-linked polymer that is comprised in the dry layer comprises unreacted electrophilic groups. Suitable solvents are as defined herein before. In a preferred embodiment, the first and second solvent are miscible, in a more preferred embodiment the first and second solvent are the same.

In case the second liquid contains a buffering system, the second liquid preferably has a buffering pH in the range of 7 to 11, more preferably in the range of 8 to 10. The buffer capacity of the second liquid preferably is at least 10 mmol·l$^{-1}$·pH$^{-1}$. More preferably, the buffer capacity is a least 25 mmol·l$^{-1}$·pH$^{-1}$, most preferably the buffer capacity is at least 50 mmol·l$^{-1}$·pH$^{-1}$.

Another aspect of the invention relates to an adhesive haemostatic product selected from a coated mesh, a coated foam or a coated powder, said haemostatic product comprising:
a porous solid substrate having a porosity of at least 20 vol. % and comprising an outer surface that comprises a nucleophilic polymer containing reactive nucleophilic groups;
an adhesive coating that covers at least a part of the solid substrate, said coating comprising EL-POX containing on average at least 1 reactive electrophilic group.

This adhesive haemostatic product may suitably be obtained by the process described herein before.

As explained herein before, the haemostatic product has excellent adhesive properties due to the presence of electrophilic reactive groups that are capable of reacting with nucleophilic groups that are naturally present in tissue. In addition, this haemostatic product offers the advantage that upon contact with blood or other aqueous fluids, the adhesive coating will be anchored to the porous substrate as reactive electrophilic groups in the EL-POX will react with reactive nucleophilic groups of the nucleophilic polymer under the formation of covalent bonds.

The EL-POX present in the coating of the adhesive haemostatic material may be covalently bound to the porous solid substrate. Furthermore, the EL-POX may be cross-linked. Preferred forms of the porous solid substrate, the EL-POX and the nucleophilic polymer have been described herein before.

The EL-POX in the coating of the haemostatic product preferably contains 5 reactive electrophilic groups, more preferably 25 reactive electrophilic groups and most preferably 50 reactive electrophilic groups.

The substrate typically represents at least 10 wt. %, more preferably at least 50 wt. % and most preferably at least 75 wt. % of the haemostatic product.

The EL-POX containing coating typically represents 5-75 wt. % of the haemostatic product. More preferably, the coating represents 10-50 wt. %, most preferably 12-25 wt. % of the haemostatic product.

The coating preferably contains 25-100 wt. % of EL-POX. More preferably, the EL-POX content of the coating is at least 50 wt. %, most preferably at least 75 wt. %.

The present invention enables the preparation of coated haemostatic products wherein the adhesive coating contains pores that are interconnected with the pores of the porous solid substrate.

According to a particularly preferred embodiment, the adhesive haemostatic has a pore density of at least 50%, more preferably of at least 80%

The invention is further illustrated by the following non-limiting examples.

EXAMPLES

Example 1

NHS-side chain activated poly[2-(propyl/NHS-ester-ethyl)-2-oxazoline] copolymer, containing 25% NHS ester (=EL-POX, 25% NHS) units was synthesized as follows: A poly[2-(propyl/methoxy-carbonyl-ethyl)-2-oxazoline] copolymer (Degree of polymerization=DP=around 100) was synthesized by making use of cationic ring opening polymerization (CROP) using 75% 2-n-propyl-2-oxazoline (nPropOx) and 25% 2-methoxycarbonyl-ethyl-2-oxazoline (MestOx). A statistical copolymer containing 25% 2-methoxycarbonyl-ethyl groups ($^1$H-NMR) was obtained. The polymer containing 25% 2-methoxycarbonyl-ethyl groups, was hydrolyzed using sodium hydroxide (1M), yielding a copolymer with 25% 2-carboxy-ethyl-groups ($^1$H-NMR). The 2-carboxy-ethyl-groups were activated by N-hydroxysuccinimide (NHS) and diisopropylcarbodiimide (DIC), yielding a 2-(propyl/NHS-ester-ethyl)-2-oxazoline] copolymer (=EL-POX, 25% NHS). The polymer contained 25% NHS-ester groups according to $^1$H-NMR and UV-spectroscopy.

Bovine collagen sponges were prepared according to the procedure described in Faraj et al., Tissue Engineering, 2007, 13, 10, 2387-2394. The collagen was extracted from the tendon of a cow. The collagen sponges so obtained had a porosity of 95% to 98% and average pore sizes of 80-100 µm. The porosity was calculated by comparing the density of a collagen film (without void spaces) with the density of the collagen sponges. The pore sizes were determined using scanning electron microscopy according to the method described in Faraj et al., Tissue Engineering, 2007, 13, 10, 2387-2394.

The EL-POX, 25% NHS was dissolved in acetone (180 mg/ml). The solution was evenly distributed drop wise on top of the freeze dried bovine collagen sponges. Immediately after coating, the sponges were dried at room temperature under vacuum (1 mbar) for 8 hours. Adhesive collagen sponges with an EL-POX, 25% NHS coating (15 mg/cm$^2$) were obtained.

To assess possible cross-linking between the EL-POX, 25% NHS and the nucleophilic amine groups present on the collagen, the coated collagen sponge was rinsed with acetone. All EL-POX, 25% NHS was recovered in the acetone extract, indicating that the electrophilic groups in the EL-POX had not reacted with the amine groups in the collagen during coating and/or drying.

The haemostatic properties of the coated collagen sponges were assessed as follows:
- 100 µL of fresh heparinized whole blood was added drop wise on top of the EL-POX, 25% NHS coated side of a collagen sponge.
- Another EL-POX, 25% NHS coated sponge was placed on top of the blood coated collagen sponge, with the EL-POX coated side facing the blood ('sandwich method').
- Mild pressure was applied for 10 seconds using a gauze. Next, the sandwich was put in beaker containing water and the water was stirred for two minutes. The two collagen sponges remained adhered under these conditions and no blood leaked from the sponges, indicating haemostasis and adhesion.

In a control experiment using non-coated collagen sponges, the sponges detached after 20 seconds under water and the water turned red, indicating absence of haemostasis.

Example 2

NHS-side chain activated poly 2-(propyl/hydroxy-ethyl-amide-ethyl/NHS-ester-ethyl-ester-ethyl-amide-ethyl)-2-oxazoline] terpolymer containing 15% NHS-ester groups (=EL-POX, 15% NHS) was synthesized as follows:

Poly[2-(propyl/methoxy-carbonyl-ethyl)-2-oxazoline] copolymer (DP=+/−100) was synthesized by means of CROP using 70% 2-propyl-2-oxazoline and 30% 2-metoxy-carbonyl-ethyl-2-oxazoline. A statistical copolymer containing 30% 2-methoxycarbonyl-ethyl groups ($^1$H-NMR) was obtained. Secondly, the polymer containing 30% 2-methoxycarbonyl-ethyl groups, was reacted with ethanolamine yielding a copolymer with 30% 2-hydroxy-ethyl-amide-ethyl-groups ($^1$H-NMR). After that, part of the 2-hydroxy-ethyl-amide-ethyl-groups was reacted with succinic anhydride yielding a terpolymer with 70% 2-propyl groups, 15% 2-hydroxy-ethyl-amide-ethyl-groups and 15% 2-carboxy-ethyl-ester-ethyl-amide-ethyl-groups according to $^1$H-NMR. Lastly, the 2-carboxy-ethyl-ester-ethyl-amide-ethyl-groups were activated by N-hydroxysuccinimide (NHS) and diisopropylcarbodiimide (DIC), yielding EL-POX, 15% NHS. The polymer contained 15% NHS-ester groups according to $^1$H-NMR.

The EL-POX, 15% NHS (130 mg) and anhydrous sodium borate (47 mg) were weighed and a solution of isopropanol/2-butanone (1.6 mL, v/v, 1:1) was added, resulting in a fine suspension as the anhydrous sodium borate is insoluble in isopropanol/2-butanone (v/v, 1:1). The suspension was evenly distributed drop wise on top of the freeze dried bovine collagen sponges. Immediately after coating, the sponges were dried at room temperature under vacuum (1 mbar) for 8 hours. Adhesive collagen sponges with an EL-POX, 15% NHS and an anhydrous sodium borate coating (19 mg/cm$^2$) were obtained.

The haemostatic properties of the coated collagen sponges of were assessed as follows:
- 100 µL of fresh heparinized whole blood was added drop wise on top of the EL-POX, 15% NHS and an anhydrous sodium borate coated side of a collagen sponge.
- Another EL-POX, 15% NHS and an anhydrous sodium borate coated sponge was placed on top of the blood coated collagen sponge, with the EL-POX coated side facing the blood ('sandwich method').

Mild pressure was applied for 10 seconds using a gauze. Next, the sandwich was put in beaker containing water and the water was stirred for three minutes.

The two collagen sponges remained adhered under these conditions and no blood leaked from the sponges, indicating haemostasis and adhesion.

Example 3

In this example several polymers were tested for shear strength, an overview of the samples is provided in Table 1. Polymers (DP=+/−100) were synthesized with CROP of 2-n-propyl-2-oxazoline, 2-ethyl-2-oxazoline and 2-methoxy-ethyl-2-oxazoline. The EL-POX used as sample 1-3, were post modified via the route described in example 1. The EL-POX used as sample 4-6 were synthesized via the route described in example 2. All activated polymers were analyzed via $^1$H-NMR and UV-spectroscopy for NHS content. PEG 4-arm NHS (Pentaerythritol poly(ethyleneglycol) ether tetrasuccinimidyl glutarate, sample 7) was obtained from NOF America corporation. Bovine collagen sponges (5×7×1 cm (b×l×h)) were tested as a control (sample 8). All coated sponges were prepared as described in Example 1.

Preparation Procedure

Porous collagen sponges were weighed (n=7).

EL-POX solutions were prepared by dissolving a defined amount of polymer in organic solvent (dichloromethane (DCM)/isopropylalcohol (IPA) (v/v, 1:1)) to a final concentration of 300 mg/mL.

The EL-POX solution was coated dropwise on a part of the porous collagen sponges (14 cm$^2$) to obtain the aimed coating density of 15 mg/cm$^2$. The coated porous collagen sponges were dried overnight in a vacuum oven (5 mbar) at room temperature.

The coated porous collagen sponges were weighed again and the coating density was determined. An overview of the used polymers and coating densities are provided in Table 1.

Test Procedure

These polymers were tested for shear strength in the following way:

The constructs were cut into equal pieces of 5×1 cm (b×l).

The coated sides were put together with the adhesive sides facing each other using 200 μL of heparinized human blood. A weight (10 g) was applied for 10 seconds for a standardized pressure.

The constructs were allowed to crosslink for defined times: 1 minute (t1) or 15 minutes (t15).

At the defined time points the constructs were positioned in a shear tester (Zwicky Roell, 20 N load cell) and shear strength was measured until failure.

Output: The measured force (N) is divided by the overlapping area of the constructs (cm$^2$) resulting in the shear strength (in kPa). The results are listed in Table 1.

TABLE 1

Results of shear strength test

| | | Coating density (mg/cm2) n = 7 | Shear strength (kPa) n = 6 t1 and t15 | |
|---|---|---|---|---|
| Sample | EL-POX | Average | t1 | t15 |
| 1 | P(PropOx-EtOx-NHS) (50-40-10) | 14.5 ± 0.8 | 2.10 ± 1.64 | 5.29 ± 1.44 |
| 2 | P(PropOx-EtOx-NHS) (40-35-25) | 14.0 ± 0.9 | 3.20 ± 1.53 | 8.29 ± 1.11 |
| 3 | P(PropOx-EtOx-NHS) (40-50-10) | 14.5 ± 0.4 | 1.91 ± 0.85 | 4.62 ± 0.60 |
| 4 | P(PropOx-OH-NHS) (70-20-10) | 14.2 ± 2.9 | 3.45 ± 0.43 | 5.27 ± 1.26 |
| 5 | P(PropOx-OH-NHS) (70-5-25) | 15.1 ± 1.3 | 2.98 ± 0.43 | 8.20 ± 2.16 |
| 6 | P(PropOx-OH-NHS) (50-40-10) | 14.6 ± 0.8 | 1.29 ± 0.60 | 4.79 ± 1.74 |
| Comparative examples | | | | |
| 7 | PEG 4-arm NHS | 13.0 ± 1.5 | 3.18 ± 0.32 | 6.78 ± 1.42 |
| 8 | Collagen without coating | — | 0.79 ± 0.48 | 1.47 ± 0.46 |

From these results can be concluded that:

the EL-POX polymers (1-6) show higher shear strength with increasing crosslinking times.

EL-POX polymers (2 and 5) show higher shear strength values than polymer PEG 4-arm NHS (7) at t15.

Control sample (8) shows limited to no shear strength, indicating that the crosslinking is caused by the NHS-ester groups.

This example illustrates that EL-POX coated on collagen is capable to crosslink in the presence of blood creating higher shear strength than the same concentration of PEG 4-arm NHS coated on collagen.

Example 4

NHS-side chain activated poly 2-(propyl/hydroxy-ethyl-amide-ethyl/NHS-ester-ethyl-ester-ethyl-amide-ethyl)-2-oxazoline] terpolymer containing 20% NHS-ester groups (=EL-POX, 20% NHS) was synthesized as follows:

Poly[2-(propyl/methoxy-carbonyl-ethyl)-2-oxazoline] copolymer (DP=+/−100) was synthesized by means of CROP using 70% 2-propyl-2-oxazoline and 30% 2-methoxycarbonyl-ethyl-2-oxazoline. A statistical copolymer containing 30% 2-methoxycarbonyl-ethyl groups ($^1$H-NMR) was obtained. Secondly, the polymer containing 30% 2-methoxycarbonyl-ethyl groups, was reacted with ethanolamine yielding a copolymer with 30% 2-hydroxy-ethyl-amide-ethyl-groups ($^1$H-NMR). Next, part of the 2-hydroxy-ethyl-amide-ethyl-groups were reacted with succinic anhydride yielding a terpolymer with 70% 2-propyl groups, 10% 2-hydroxy-ethyl-amide-ethyl-groups and 20% 2-carboxy-ethyl-ester-ethyl-amide-ethyl-groups according to $^1$H-NMR. Lastly, the 2-carboxy-ethyl-ester-ethyl-amide-ethyl-groups were activated by N-hydroxysuccinimide (NHS) and diisopropylcarbodiimide (DIC), yielding EL-POX, 20% NHS. The polymer contained 20% NHS-ester groups according to $^1$H-NMR.

Amine functionalized NU-POX containing propyl and amine groups in the alkyl side chain were synthesized by CROP of nPropOx and MestOx and subsequent amidation of the methyl ester side chains with ethylene diamine to yield a poly(2-propyl/aminoethylamidoethyl-2-oxazoline) copolymer (NU-POX). The polymer contained 20% $NH_2$ according to $^1$H-NMR.

Bovine collagen sponges (7×5×1 cm) were used, which were prepared as described in Example 1. For these experiments, an ExactaCoat SC ultrasonic spraying device (Sono-Tek) equipped with a heating plate was used to coat the collagen sponges.

Test 4A: EL-POX in Solution

A solution of EL-POX (EL-POX, 20% NHS) in IPA/2-butanone (v/v, 1:1) (90 mg/mL) was homogeneously distributed onto the collagen by ultrasonic spraying, according to the settings shown in Table 2, leading to a coating density of 5 mg/cm$^2$. SEM-images showed that the porous structure of the collagen was maintained.

The constructs were cut in pieces (2 cm$^2$) and tested using the shear strength test at t15 as described in example 3. The results were 10.9+/−3.3 kPa (n=4), indicating good adhesion and hemostasis.

TABLE 2

| Parameters ultrasonic spraying | |
| --- | --- |
| Nozzle | 48 Accumist |
| Substrate Description | Collagen Bovine Type 1 |
| Coating Area (cm) | 5 × 7 cm |
| Nozzle Power/Idle Power | 6 in test 4A \| |
| | 3 in test 4B-4D \| |
| Dispense rate (ml/min) | 1 ml/min |
| Pressure (mbar) | 40 mbar |
| Trans Speed (mm/sec) | 20 mm/s for example 5A, 5B, 5C |
| | (NU-POX coating) \| |
| | 40 mm/s for example 5C |
| | (EL-POX coating) and 5D \| |
| Height from top of substrate (mm) | 30 mm |
| Spacing (mm) | 5 mm |
| Coating cycles | 2 coating cycles for test 4A \| |
| | 3 coating cycles for test 4B \| |
| | 1 coating cycles for tests 4C and 4D \| |

Test 4B: EL-POX with Suspended Buffer

A solution of EL-POX in IPA/2-butanone (v/v, 1:1) (10 mg/mL) with suspended HEPES-buffer (1.7 g) was homogeneously distributed onto the collagen by ultrasonic spraying, according to the settings shown in table 2, leading to a coating density of 5 mg/cm$^2$. SEM-images showed that the porous structure of the collagen was maintained. The constructs were cut in pieces (2 cm$^2$) and tested using the shear strength test at t15 as described in example 3. The average shear strength measured was 2.6+/−0.8 kPa (n=3), indicating good adhesion and hemostasis.

Test 4C: (1) Solution of NU-POX and Buffer+(2) Solution of EL-POX

A solution of NU-POX in water (10 mg/mL) with HEPES (1.7 g) was homogeneously distributed onto the collagen by ultrasonic spraying, according to the settings shown in table 2. The solvent was allowed to evaporate for 30 min. After this, a solution of EL-POX in IPA/2-butanone (v/v, 1:1) (15 mg/mL) was homogeneously distributed by ultrasound spraying, according to the settings displayed in table 2, on top of the coated collagen. After coating, a coating density of 5 mg/cm$^2$ (+40 wt. % NU-POX and +60 wt. % EL-POX) was obtained. SEM-images showed that the porous structure of the collagen was maintained. The constructs were cut in pieces (2 cm$^2$) and tested using the shear strength test at t15 as described in example 3. The average shear strength measured was 3.9+/−2.9 kPa (n=2), indicating good adhesion and hemostasis.

Test 4D: Solution of Buffer (Suspension of EL-POX)

A suspension EL-POX in IPA/diethylether/triethylamine (v/v/v, 50:50:1) was homogeneously distributed onto the collagen by ultrasonic spraying according to the settings shown in table 2. After coating a coating density of 4 mg/cm$^2$ was obtained. SEM-images showed that the porous structure of the collagen was maintained. The constructs were cut in pieces (2 cm$^2$) and tested using the shear strength test as described in example 3. The average shear strength measured was 4.2+/−3.5 kPa (n=3), indicating good adhesion and hemostasis.

In addition, the haemostatic properties of the ultrasonically coated collagen sponges 4A-4D were assessed as follows:

100 μL of fresh heparinized whole blood was added drop wise on top of the EL-POX coated side of a collagen sponge.

Another EL-POX coated sponge was placed on top of the blood coated collagen sponge, with the EL-POX coated side facing the blood ('sandwich method').

Mild pressure was applied for 10 seconds using a gauze. Next, the sandwich was put in beaker containing water and the water was stirred for two minutes.

The two collagen sponges 4A-4D all remained adhered under these conditions and no blood leaked from the sponges, indicating haemostasis and adhesion.

Example 5

NHS-side chain activated poly 2-(propyl/hydroxy-ethyl-amide-ethyl/NHS-ester-ethyl-ester-ethyl-amide-ethyl)-2-oxazoline] terpolymer (=EL-POX, 20% NHS) was synthesized as described in example 2.

The EL-POX, 20% NHS was dissolved in methanol (180 mg/ml). The solution was evenly distributed drop wise on top of an Oxidized Regenerated Cellulose patch (ORC, Gelita-Cel). Immediately after coating, the patches were dried at room temperature under air flow for 4 hours. ORC with an EL-POX, 20% NHS coating (12 mg/cm$^2$) were obtained.

The haemostatic properties of the coated ORC were assessed as follows:

100 μL of fresh heparinized whole blood was added drop wise on top of the EL-POX, 20% NHS coated side of ORC (1×1 cm).

Another EL-POX, 20% NHS coated ORC was placed on top of the blood coated ORC, with the EL-POX coated side facing the blood ('sandwich method').

Mild pressure was applied for 10 seconds using a gauze. Next, the sandwich was put in beaker containing water and the water was stirred for five minutes. The two ORC pieces remained adhered under these conditions for five minutes and the medium did not turn red.

In a control experiment using non-coated ORC, ORC detached within a minute under water during stirring and the water turned red, indicating absence of hemostasis.

Example 6

NHS-side chain activated poly 2-(propyl/hydroxy-ethyl-amide-ethyl/NHS-ester-ethyl-ester-ethyl-amide-ethyl)-2-oxazoline] terpolymer (=EL-POX, 20% NHS) was synthesized as described in example 2. Chitosan powder was obtained from Sigma-Aldrich. (degree of deacetylation 75-85%, Mn 10,000). Starch powder (HaemoCer®) was obtained from BioCer, Germany.

Powders were coated separately with EL-POX, 20% NHS (EL-POX) in the following way.

Powder (chitosan or starch) was weighed and coated with a solution of EL-POX (15 mg/mL) in DCM.
The suspension was dried under reduced pressure.
After this, the dried coated powder was grinded forming a homogenously fine powder. The coated chitosan powder contains about 25 wt. % EL-POX. The coated starch powder contains about 10 wt. % EL-POX.

As controls, grinded uncoated chitosan powder, grinded uncoated starch powder and grinded EL-POX were tested.

The EL-POX coated powders and the control samples were mixed with (1) carbonate buffer (0.1 M, pH 9) or (2) heparinized human blood (pH 7.4) to assess the heamostatic properties. This was tested in the following way: the powders were weighed in an Eppendorf tube and mixed with 250 µL of buffer (1) or blood (2). Gelation time was determined by inverting the tube up and down until a gel was formed.

The amount of materials used and the results of the crosslink tests are given in Table 3.

TABLE 3

Results of crosslinking tests

| sample | Chitosan* (mg) | Starch* (mg) | EL-POX* (mg) | (1) Buffer pH 9 (µL) | (2) blood (µL) | gel time |
|---|---|---|---|---|---|---|
| 1 | 16.5 | | 5.7 | | 250 | 2 min |
| 2 | 17.2 | | 5.8 | 250 | | 1 min |
| 3 | 19.8 | | | 250 | | No gel |
| 4 | 18.0 | | | | 250 | No gel |
| 5 | | | 20.1 | | 250 | 45 sec |
| 6 | | | 24 | 250 | | No gel |
| 7 | | 18.1 | 2.0 | 250 | | No gel |
| 8 | | 20 | | | 250 | No gel |
| 9 | | 21 | | 250 | | No gel |
| 10 | | 17.8 | 2.0 | | 250 | 2 min |

*calculated from the wt % EL-POX in the coated powders

These results show that chitosan is able to crosslink with EL-POX (sample 2) and that starch is not able to crosslink with EL-POX (sample 7). Both, chitosan and starch coated with EL-POX were capable of crosslinking with blood (samples 1 and 10) while the non-coated chitosan and starch powders did not form a gel in the presence of buffer and/or blood (samples 3, 4, 8 and 9). EL-POX powder was capable of forming a gel by reacting with amines in blood (sample 5), whereas no gel-formation was observed when the EL-POX powder was combined with buffer (sample 6).

Gels containing EL-POX were found to be stable under water. In contrast thereto blood gels prepared by adding 200 mg starch or chitosan to 250 µL blood, were not stable under water.

Example 7

NHS-side chain activated poly 2-(propyl/hydroxy-ethyl-amide-ethyl/NHS-ester-ethyl-ester-ethyl-amide-ethyl)-2-oxazoline] terpolymer (=EL-POX, 20% NHS) was synthesized as described in example 3. PEG 4-arm NHS (Pentaerythritol poly(ethyleneglycol)ether tetrasuccinimidyl glutarate, EL-PEG) was obtained from NOF America corporation. Bovine collagen sponges (7×5×1 cm) were prepared as described in Example 1.

Two application methods were compared: (I) melt method and (II) coating liquid method.

(I) Melt Method (Comparative Examples)

A known amount of polymer powders, EL-POX, 20% NHS and EL-PEG, were homogenously distributed on top of the collagen sponges to obtain the coating densities indicated in table 4. EL-POX, 20% NHS and EL-PEG were heated at the temperatures indicated in Table 4, in a preheated oven for 5 min to melt the polymer powder. Within this time frame and temperature setting, both EL-POX and EL-PEG remained stable.

SEM-images of the prepared constructs showed that the formed polymer film sealed off the porous structure of the collagen top layer.

TABLE 4

Settings (I) melt method

| Polymer | Temperature oven (° C.) | Coating density (mg/cm$^2$) |
|---|---|---|
| EL-POX, 20% NHS | 140 | 12 |
| EL-PEG | 60 | 11 |

(II) Coating Liquid Method

EL-POX, 20% NHS powder was dissolved in IPA/DCM (v/v, 1:1) (15 mg/mL) and the solution was distributed evenly on top of the collagen sponges by drip coating, to obtain a coating density of 12 mg/cm$^2$. The sponges were dried in a vacuum oven for 2 hours. SEM-images showed that the porous structure of the collagen was maintained.

The haemostatic properties of the coated collagen sponges were assessed as follows:
100 µL of fresh heparinized whole blood was added drop wise on top of the EL-POX, 20% NHS or EL-PEG coated side of a collagen sponge.
Another coated sponge was placed on top of the blood coated collagen sponge, with the coated sides facing the blood ('sandwich method').
Mild pressure was applied for 10 seconds using a gauze.
Next, the sandwich was put in beaker containing water and the water was stirred for one minute.

The collagen sponges prepared by melting (both EL-POX and EL-PEG), detached within a minute indicating absence of haemostasis and adhesion. The collagen sponges (with EL-POX) prepared by drip coating remained adhered during 1 minute indicating haemostasis and adhesion.

This example shows that the application method affects the accessibility of the pores in the collagen and explains the difference in haemostasis and adhesion between the sponges obtained by melting and the sponges obtained by coating with liquid.

Example 8

Treatment of traumatic liver and spleen rupture is a major challenge for a surgeon. Since the spleen has an excellent blood supply and rupture of the spleen is often associated with massive abdominal hemorrhage.

Standardized combined penetrating spleen rupture was inflicted in n=1 anesthetized swine (Domestic Pig, Male, Body Weight Range: 40 kg, Adult). A midline laparotomy was performed to access the spleen. Using a scalpel, n=3 (S1 . . . S3) subcapsular standardized lesions (10 mm×10 mm) were made.

Three types of haemostatic products were tested, an overview is provided in Table 5.

TABLE 5

Description of tested products

| Sample | Product | Description of Product |
|---|---|---|
| S1 | EL-POX | Collagen sponge coated with EL-POX, 25% NHS (5 mg/cm$^2$), prepared as in Example 4 Comparative examples |
| S2 | No coating | Bovine collagen sponge, prepared as in Example 1 |
| S3 | Reference | 2 × 2 cm Hemopatch ™ (obtained from Baxter Healthcare) |

The heamostatic products were applied with gentle pressure. After application of the product the time to haemostasis was assessed, see Table 6.

TABLE 6

Results animal model

| Sample | Product applied | Result |
|---|---|---|
| S1 | EL-POX | TTH: 1 minute, n = 1 |
| | Comparative examples | |
| S2 | No coating | TTH: 3 to 4 minutes, n = 2 |
| S3 | Reference | TTH: 1 minute, n = 1 |

TTH = time to haemostasis;
n = no. of products needed to reach hemostasis

This example shows the haemostatic efficacy of the EL-POX coated sponge on the spleen of a pig. Based on the end points in Table 6, the EL-POX coated sponge performed equally well in this model in obtaining hemostasis as the reference product (Hemopatch™) and better than the control. Furthermore, it was observed that the blood absorption capacity of the EL-POX coated sponge was superior to that of the reference product. Thus, hemostasis achieved with the EL-POX coated sponge was aided by a rapid onset of blood coagulation.

The invention claimed is:

1. An adhesive haemostatic product selected from a coated mesh, a coated foam or a coated powder, the haemostatic product comprising:
    a) porous solid substrate having a porosity of at least 5 vol. % and comprising an outer surface that comprises a nucleophilic polymer comprising reactive nucleophilic groups;
    b) an adhesive coating that covers at least a part of the solid substrate, the coating comprising an electrophilically activated polyoxazoline (EL-PDX), the polyoxazoline being a polymer of 2-alkyl-2-oxazoline selected from 2-methyl-2-oxazoline, 2-ethyl-2-oxazoline, 2-propyl-2-oxazoline, 2-butyl-2-oxazoline and combinations thereof, and the polyoxazoline being electrophilically activated by the presence of at least 5 reactive electrophilic groups, wherein, in the presence of water, the electrophilic groups of the EL-PDX react with amine groups naturally present in tissue, to form covalent bonds and wherein, upon contact with blood, the electrophilic groups of the EL-PDX react with the reactive nucleophilic groups of the nucleophilic polymer to form covalent bonds.

2. The adhesive haemostatic product according to claim 1, wherein the porous solid substrate has a porosity of at least 50 vol. %.

3. The adhesive haemostatic product according to claim 1, wherein the EL-PDX contains on average at least 10 reactive electrophilic groups.

4. The adhesive haemostatic product according to claim 1, wherein the reactive electrophilic groups are selected from carboxylic acid esters, sulfonate esters, phosphonate esters, pentafluorophenyl esters, p-nitrophenyl esters, p-nitrothiophenyl esters, acid halide groups, anhydrides, ketones, aldehydes, isocyanato, thioisocyanato, isocyano, epoxides, activated hydroxyl groups, glycidyl ethers, carboxyl, succinimidyl ester, succinimidyl carbonate, succinimidyl carbamates, sulfosuccinimidyl ester, sulfosuccinimidyl carbonate, imido esters, dihydroxyphenylalanine, 3,4-dihydroxyphenylalanine (DOPA), dopamine, 3,4-dihydroxyhydroccinamic acid (DOHA), norepinephrine, epinephrine, catechol and combinations thereof.

5. The adhesive haemostatic product according to claim 4, wherein the reactive electrophilic groups are selected from isocyanato, thioisocyanato, succinimidyl ester, sulfosuccinimidyl ester, and combinations thereof.

6. The adhesive haemostatic product according to claim 1, wherein the EL-PDX is non-crosslinked.

7. The adhesive haemostatic product according to claim 1, wherein the porous solid substrate represents at least 50 wt. % of the haemostatic product.

8. The adhesive haemostatic product according to claim 1, wherein the EL-PDX containing coating represents 5-50 wt. % of the haemostatic product.

9. The adhesive haemostatic product according to claim 1, wherein the adhesive coating contains 25-100 wt. % of EL-PDX.

10. The adhesive haemostatic product according to claim 1, wherein at least a part of the EL-PDX is covalently bound to the porous solid substrate.

11. The adhesive haemostatic product according to claim 1, wherein the EL-PDX has an average molecular weight in the range of 1,000 to 100,000 g/mol and wherein the EL-PDX contains 3 to 50 pendant electrophilic groups per 100 monomers.

12. The adhesive haemostatic product according to claim 1, wherein the nucleophilic polymer is selected from the group consisting of protein, chitosan, synthetic polymers, and carbohydrate polymers; and in which the reactive nucleophilic groups are selected from the group consisting of amine, thiol, phosphine and combinations thereof.

13. The adhesive haemostatic product according to claim 1, wherein the porous solid substrate is a powder having a mass weighted average particle size in the range of 10-200 µm.

14. The adhesive haemostatic product according to claim 13, wherein the powder has a mass weighted average particle size in the range of 25-100 µm.

15. The adhesive haemostatic product according to claim 13, wherein the powder comprises gelatin and/or polysaccharide.

16. The adhesive haemostatic product according to claim 15, wherein the powder comprises gelatin.

17. The adhesive haemostatic product according to claim 1, wherein, wherein the porous solid substrate is a mesh or a foam in the form of a sheet with a length of 10 to 200 mm, a width of 5 to 200 mm and a thickness of 0.5 to 10 mm.

18. The adhesive haemostatic product according to claim 17, wherein the porous solid substrate is a mesh.

19. The adhesive haemostatic product according to claim 18, wherein the mesh is a sheet or a gauze made from woven or non-woven fibres.

20. The adhesive haemostatic product according to claim 19, wherein the fibres contained in the mesh are made of gelatin, collagen, oxidized regenerated cellulose (ORC) or a combination thereof.

\* \* \* \* \*